(12) United States Patent
Saito

(10) Patent No.: US 8,647,318 B2
(45) Date of Patent: Feb. 11, 2014

(54) UNDERPANTS-TYPE DISPOSABLE DIAPER

(75) Inventor: Kyota Saito, Kagawa-ken (JP)

(73) Assignee: Uni-Charm Corporation, Shikokuchuo-Shi, Ehime-Ken (JP)

( * ) Notice: Subject to any disclaimer, the term of this patent is extended or adjusted under 35 U.S.C. 154(b) by 245 days.

(21) Appl. No.: 12/538,812

(22) Filed: Aug. 10, 2009

(65) Prior Publication Data

US 2009/0299320 A1    Dec. 3, 2009

Related U.S. Application Data

(63) Continuation of application No. 11/235,538, filed on Sep. 27, 2005, now abandoned.

(30) Foreign Application Priority Data

Oct. 1, 2004    (JP) .................................. 2004-289868

(51) Int. Cl.
*A61F 13/20* (2006.01)

(52) U.S. Cl.
USPC .................................................... 604/385.27

(58) Field of Classification Search
USPC ...................... 604/358, 385.01, 385.24–385.3
See application file for complete search history.

(56) References Cited

U.S. PATENT DOCUMENTS

| | | | |
|---|---|---|---|
| 4,743,241 A | 5/1988 | Igaue et al. | |
| 5,147,343 A | 9/1992 | Kellenberger | |
| 5,415,649 A | 5/1995 | Watanabe et al. | |
| 5,601,542 A | 2/1997 | Melius et al. | |
| 5,836,931 A * | 11/1998 | Toyoda et al. | 604/385.29 |
| 5,940,887 A * | 8/1999 | Rajala et al. | 2/243.1 |
| 6,217,563 B1* | 4/2001 | Van Gompel et al. | 604/385.101 |
| 6,497,695 B1 | 12/2002 | Bruemmer-Prestley et al. | |
| 7,018,369 B2 | 3/2006 | VanGompel et al. | |
| 7,118,558 B2* | 10/2006 | Wu et al. | 604/385.29 |
| 7,150,731 B2 | 12/2006 | Cazzato et al. | |

(Continued)

FOREIGN PATENT DOCUMENTS

| | | |
|---|---|---|
| EP | 1374814 A1 | 1/2004 |
| JP | 62-21802 | 1/1987 |

(Continued)

OTHER PUBLICATIONS

Extended European Search Report for EP05787933 issued Mar. 25, 2010.

(Continued)

*Primary Examiner* — Jackie Ho
*Assistant Examiner* — Bradley Philips
(74) *Attorney, Agent, or Firm* — Lowe Hauptman & Ham LLP

(57) ABSTRACT

An underpants-type disposable diaper is of a size and a water absorption capacity suitable for infants 3 to 6 years old, and is capable of preventing the protrusion of the groin portion of the diaper in use so that leakage does not occur. The leakage can be avoided by increasing the size and the water absorption capacity of the diaper main body to a level suitable for infants 3 to 6 year olds still using diaper and at the same time improving the tracks of a plurality of elastic members disposed along the peripheral edges of leg holes so as to reduce the elasticity in the vertical direction of the crotch section and prevent the protrusion of an infant's groin.

25 Claims, 6 Drawing Sheets

(56) References Cited

U.S. PATENT DOCUMENTS

| | | |
|---|---|---|
| 7,329,245 B2 | 2/2008 | Torigoshi et al. |
| 2002/0042600 A1* | 4/2002 | Datta et al. ............... 604/385.13 |
| 2002/0049421 A1* | 4/2002 | Hayase et al. ............ 604/385.27 |
| 2002/0143313 A1 | 10/2002 | Tsuji et al. |
| 2002/0188268 A1 | 12/2002 | Kline et al. |
| 2003/0135192 A1* | 7/2003 | Guralski et al. ............. 604/391 |
| 2003/0144645 A1* | 7/2003 | Karami ......................... 604/389 |
| 2004/0030317 A1 | 2/2004 | Torigoshi |
| 2004/0064121 A1* | 4/2004 | Van Gompel et al. ... 604/385.01 |
| 2004/0133180 A1 | 7/2004 | Mori et al. |
| 2004/0186453 A1* | 9/2004 | Shimada et al. ......... 604/385.27 |
| 2008/0071241 A1* | 3/2008 | Bittner et al. ............ 604/385.27 |
| 2009/0048573 A1* | 2/2009 | Van Gompel et al. ... 604/385.29 |

FOREIGN PATENT DOCUMENTS

| | | | | |
|---|---|---|---|---|
| JP | 62/243806 | | 10/1987 | |
| JP | 8182703 A | | 7/1996 | |
| JP | 2571282 B2 | | 10/1996 | |
| JP | 10-127687 | | 5/1998 | |
| JP | 11-262503 | | 9/1999 | |
| JP | 2000014700 A | | 1/2000 | |
| JP | 2000237233 A | * | 9/2000 | ............. A61F 13/15 |
| JP | 2001-000478 | | 1/2001 | |
| JP | 2001-087310 | | 4/2001 | |
| JP | 2002-172132 | | 6/2002 | |
| JP | 2002272783 A | | 9/2002 | |
| JP | 2002272784 A | | 9/2002 | |
| JP | 2002273808 A | | 9/2002 | |
| JP | 2003-102779 | | 4/2003 | |
| JP | 3422340 | | 4/2003 | |
| JP | 2004-236775 | | 8/2004 | |
| WO | 0185080 | | 11/2001 | |

OTHER PUBLICATIONS

Notice of Reasons for Rejection issued to Japanese Application No. 2004-289868 mailed Jun. 15, 2010.
Japanese Patent Office International Search Report for PCT/JP2005/017864 issued Dec. 27, 2005.

* cited by examiner

*Prior Art*

UNDERPANTS-TYPE DISPOSABLE DIAPER

CROSS REFERENCE TO THE RELATED APPLICATION

The present application is a continuation of U.S. application Ser. No. 11/235,538, filed Sep. 27, 2005, which claims priority from Japanese Patent Application No. 2004-289868, filed Oct. 1, 2004, the disclosures of which are incorporated herein by reference in their entirety.

FIELD OF THE INVENTION

The present invention relates to a leak-resistant underpants-type disposable diaper, and specifically relates to an underpants-type disposable diaper having a size and an absorption capacity usable for infants of 3 to 6 years old who are still in diapers, and capable of preventing a groin portion of the diaper from outwardly protruding in use.

RELATED ART

Recently, the quality of disposable diaper has been dramatically improved so that most infants wear disposable diapers. There are two types of disposable diapers. One is a type which opens up and has attachment tapes (tape-type), and the other is a type underpants-shaped type (underpants-type). The tape-type disposable diaper is to be fixed to the body with tape at two positions around the waist, and it is intended for relatively young babies a few months old. On the other hand, the underpants-type diaper is integrally formed like a pair of underwear pants, can be put on an infant while standing, and is intended for infants of 1 to 3 years old.

In general, infants are said to be out of diapers at around the age of 2, and it is recommended to start toilet training at this age. However, according to a recent survey in Japan, the age at which diaper use was discontinued in the daytime was 21.4 months old on average in 1960, but 30.5 months old on average in 2000, a delay of approximately up to 9 months. Thus, the discontinuation of diaper use has been delayed in recent years such that older infants use disposable diapers. Accordingly, there has been is a steady increase in the demand for the underpants-type disposable diaper because the underpants-type diaper of a large size adaptable to older infants, who have not been regarded as wearers of disposable diapers, has been demanded.

In this respect, in the conventional underpants-type diaper, there has been a problem in preventing fluid leakage due to the groin portion protruding in use, and the invention disclosed in Japanese patent number 2571282 (patent reference 1) has been cited as one tackling this problem. According to the invention described in this patent reference 1, an elastic member (hereinafter referred to as "central elastic member") is provided so that the central elastic member extends from the vicinity of a leg hole to the vicinity of the other leg hole passing across a section of the diaper positioned below the groin (hereinafter referred to as "under groin section"). In other words, in the central elastic member, both ends thereof are provided around a pair of leg holes is disposed diagonally across the under groin section thereof such that the under groin section can be lifted so as to closely adhere to its corresponding part of the body. Furthermore, both ends of the central elastic member are continuous with other elastic members (hereinafter referred to as "side elastic members") disposed along each of the leg holes. Therefore, the close contact between the diaper and the body can be maintained even when the wearer moves such as in walking, because the central elastic member can expand and contract in conjunction with the tension and shrinkage of these both side elastic members. However, in the invention according to the patent reference 1, vertical movement of the groin portion cannot be prevented, so that the problem that the groin portion protrudes in use cannot be sufficiently avoided.

SUMMARY OF THE INVENTION

The present invention has been made in view of the above-described problems and aims to provide an underpants-type disposable diaper usable for infants 3 to 6 years old who are still in diapers, and capable of preventing the groin portion from protruding while it is worn so as to provide a leak-resistant underpants-type diaper.

In at least one embodiment, the groin portion is prevented from protruding in use by careful arrangement of a plurality of elastic members disposed along the peripheral edges of the leg holes, thereby reducing the vertical movement of the groin portion even when the size and the absorption capacity of the diaper main body are increased to a level usable for infants of 3 to 6 years old. More specifically, the present invention provides the following.

(1) An underpants-type disposable diaper including an underpants-formed diaper main body, the diaper main body including an underpants-formed outer cover having a waist opening part to be fixed to a wearer's trunk, a pair of leg holes for the wearer's legs to pass thorough, a front part to be positioned ventral to the wearer, a back part to be positioned dorsal to the wearer and a crotch part jointed to the front part and the back part to be positioned between legs of the wearer, and a substantially belt-like inner member joined to the inner side of the outer cover, the inner member positioned between the leg holes; and the front part has an elastic member pulling the inner member in the lateral direction of the diaper.

In the underpants-type disposable diaper according to (1), the arrangement of a plurality of elastic members disposed along the peripheral edges of the leg holes is devised so as to prevent the protrusion of the groin portion of the diaper in use. Specifically, an elastic member pulling the inner member in the horizontal direction is provided in the front part.

(2) The underpants-type disposable diaper according to (1) in which the elastic member is a linear elastic member extending from one side edge of the front part towards the center of the front part along the peripheral edge of each of the leg holes forming a horizontally elongated arc.

According to the present invention, the elastic members are provided in the front part and the back part and each of the elastic members extends from the top front of a leg hole to the bottom rear of the leg hole to form a semicircular arc. The elastic member provided in the front part extends from the side edge of the front part toward the center of the front part forming a horizontally elongated arc, one end of which is positioned on the side edge of the front part and the other end (hereinafter referred to as "top point") is positioned near the top front of the leg hole.

(3) The underpants-type disposable diaper according to (2) in which the ratio of the minimum dimension of each elastic member from one end positioned near the side edge of the front part to the other end thereof positioned near the center of the front part in the lateral direction to the minimum dimension thereof in the vertical direction is not less than 1.0 and not more than 3.0 in a state that the elastic member is not expanded.

More specifically, the ratio of the minimum dimension of each elastic member from one end positioned at the side edge of the front part to the top point thereof in the lateral direction to the minimum dimension thereof in the vertical direction is not less than 1.0 and not more than 3.0 in a state prior to its wearing, that is to say the elastic member is not expanded. This underpants-type disposable diaper is designed so that ratios of these dimensions become larger compared to those in the conventional products which are approximately 0.5 to 0.8. That is, in this underpants-type disposable diaper, compared to the conventional products, the dimension of the elastic members in the vertical direction is small and the elastic member is horizontally elongated so as to reduce the elasticity in the vertical direction of the groin portion by pulling the groin portion in the lateral direction. Therefore, according to this underpants-type disposable diaper, the protrusion of the groin portion in use can be prevented so as to avoid fluid leakage.

(4) The underpants-type disposable diaper according to (2) or (3)

in which a plurality of the elastic member are provided in both sides of the front part; and the interval between the ends of the elastic members positioned near the center of the front part is not less than 7 mm and not more than 12 mm in a state prior to its wearing.

In the underpants-type disposable diaper according to (4), the interval between the elastic members at the top points thereof is not less than 7 mm and not more than 12 mm. Thus, in this underpants-type disposable diaper, the interval between the elastic members is designed to be wider compared to that of a conventional underpants-type disposable diaper which is about 5 mm. This underpants-type disposable diaper has been designed so as to avoid so-called rubber band traces which are apt to be formed due to the careful arrangement of a plurality of elastic members disposed along the peripheral edges of the leg holes, increasing the elasticity in the direction around the waist (in the lateral direction) and at the same time to reduce the elasticity of the groin portion in the vertical direction thereof. That is, this underpants-type disposable diaper is able to prevent the rubber band traces from being left on its wearing by widening the interval between the elastic members so as to disperse the pressure exerted on the section around the waist.

(5) The underpants-type disposable diaper according to any one of (2) to (4) in which the maximum dimension of the diaper main body in the vertical direction is not less than 225 mm and not more than 265 mm in a state prior to its wearing, while the maximum dimension thereof in the lateral direction is not less than 180 mm and not more than 215 mm in a state prior to its wearing.

In the underpants-type disposable diaper according to (5), the maximum dimension of the diaper main body in the vertical direction from the waist opening part to a bottom of the crotch part prior to its wearing is not less than 225 mm and not more than 265 mm when the maximum dimension thereof in the lateral direction is not less than 180 mm and not more than 215 mm. Even in the largest-type among the conventional products, the maximum dimension of the diaper main body in the vertical direction is about 215 mm and that in the lateral direction is about 175 mm. Accordingly, this underpants-type disposable diaper is as large as not has been observed with the conventional products, and can be worn even by infants of 3 to 6 years old who have not been regarded as wearers of diapers.

Furthermore, in the underpants-type disposable diaper of such large size, the protrusion of the groin portion is apt to become more prominent while the diaper is worn. In response, the underpants-type disposable diaper according to (5) is able to become more effective in preventing the protrusion of the groin portion in its use by the arrangement of a plurality of elastic members disposed along the peripheral edges of the leg holes so as to reduce the expansion and contraction of the groin portion in the vertical direction.

(6) The underpants-type disposable diaper according to any one of (1) to (5) in which the water absorption capacity of the absorbing body is not less than 800 g and not more than 1000 g, while the water-holding capacity thereof is not less than 500 g and not more than 700 g.

The absorbent body used in the underpants-type disposable diaper according to (6) has a larger water absorption capacity and a larger water-holding capacity than the conventional product. Specifically, in contrast to the water absorption capacity of the largest-sized conventional product which was about 660 g per diaper, the water absorption capacity of the absorbent of the underpants-type disposable diaper according to the present invention is not less than 800 g and not more than 1000 g per diaper. Furthermore, in contrast to the water-holding capacity of absorbent body of the largest-sized conventional product which is about 450 g per diaper, the water-holding capacity of the absorbent body of the underpants-type disposable diaper according to the present invention is not less than 500 g and not more than 700 g per diaper. Accordingly, the underpants-type disposable diaper of the present invention is provided with a very large water absorption capacity so as to be sufficiently usable in infants of 3 to 6 years old whose volume of urinary excretion is high.

Further, in an underpants-type disposable diaper provided with such large water absorption capacity, the protrusion of the groin portion around the crotch is apt to become more remarkable in its use. Therefore, similarly as the underpants-type disposable diaper according to (5), that according to (6) can be more effective in preventing the protrusion of the groin portion in its use by devising the arrangement of a plurality of elastic members disposed along the peripheral edges of the leg holes so as to reduce the extension and contraction of the diaper in the vertical direction of the groin portion.

According to the present invention, an underpants-type disposable diaper can be provided which has a size and a water absorption capacity usable for infants of 3 to 6 years old who are still using diapers, and is capable of preventing the protrusion of the groin portion in use so as to be resistant leakage.

DESCRIPTION OF THE PREFERRED EMBODIMENTS

In the following, the preferred embodiments of the present invention will be described with reference to the drawings.

Whole Constitution of Underpants-Type Disposable Diaper

Figure 1:
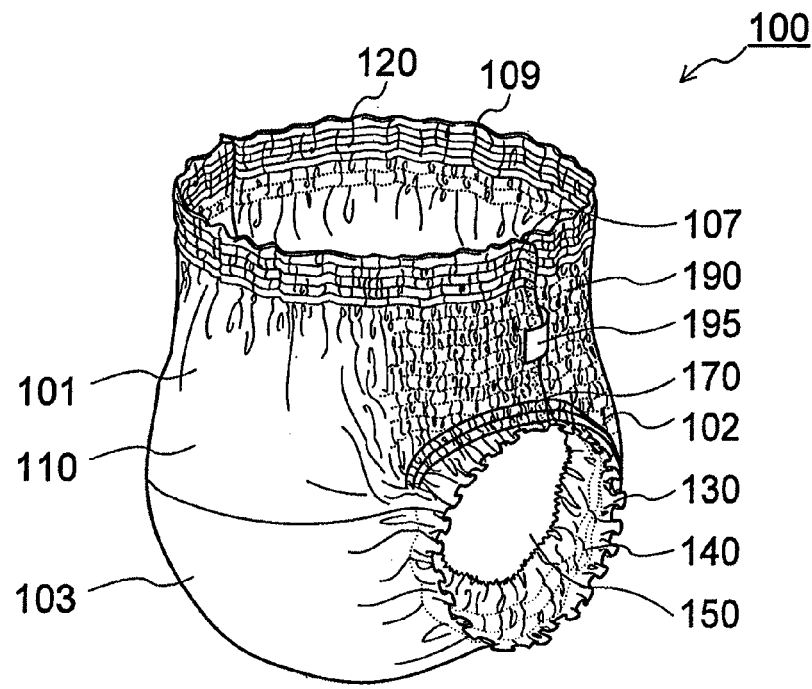
FIG. 1 is a perspective view of an underpants-type disposable diaper according to an embodiment of the present invention.
Figure 2:
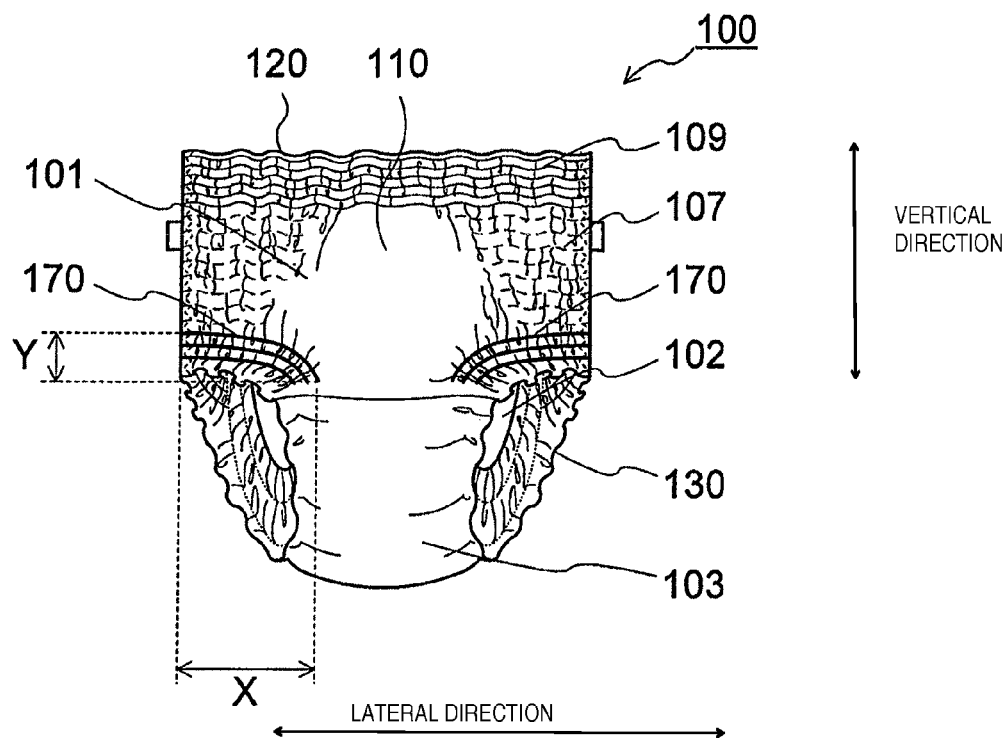
FIG. 2 is a plan view of the underpants-type disposable diaper according to an embodiment.
Figure 3:
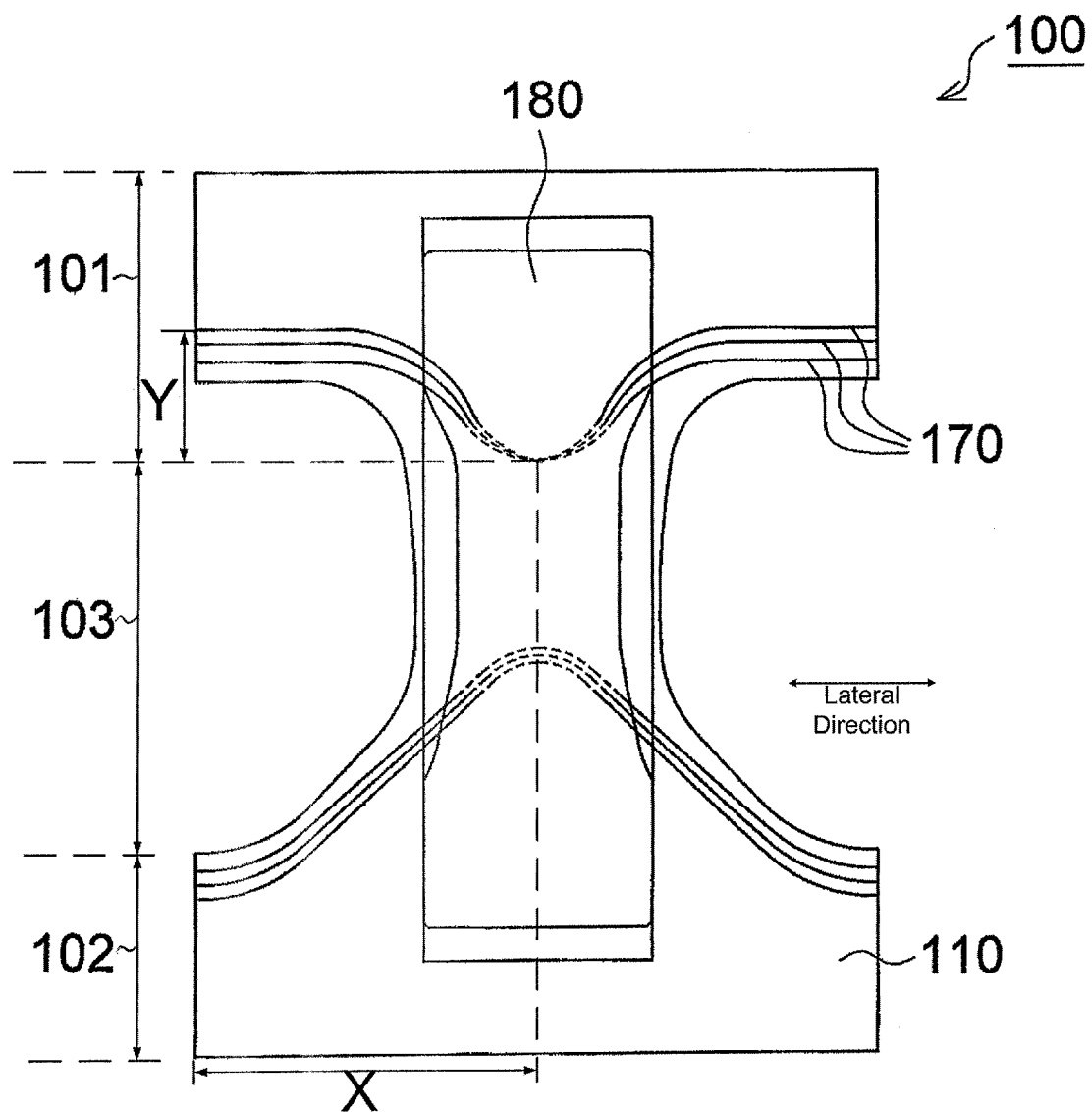
FIG. 3 is an exploded plan view of the underpants-type disposable diaper according to an embodiment whose side flap is opened to separate a front part and a back part.
Figure 6:
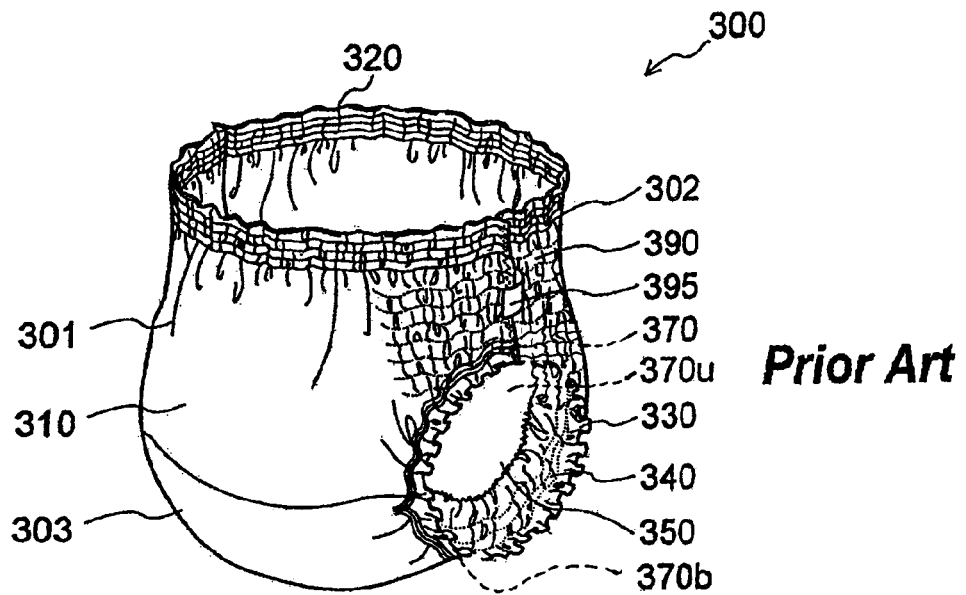
FIG. 6 is a perspective view of a conventional underpants-type disposable diaper.

FIG. 1 is a perspective view and FIG. 2 is a plan view of an underpants-type disposable diaper 100 according to an embodiment of the present invention. FIG. 3 is an exploded plan view of the underpants-type disposable diaper 100 according to this embodiment in which the side flap 190 is opened to separate a front part 101 and a back part 102. Furthermore, as a reference, a perspective view of a conventional underpants-type disposable diaper 300 is shown in FIG. 6, a plan view thereof in FIG. 7, and an exploded plan view thereof when the side flap 390 is opened) to separate a front part 301 and a back part 302 in FIG. 8. The underpants-type disposable diaper 100 according to this embodiment is wearable by infants of 3 to 6 years old, and is provided with an underpants formed diaper main body 110. As seen in FIG. 2, the underpants-type disposable diaper 100 has a vertical direction and a lateral direction which is measured side to side of the disposable diaper 100 and substantially perpendicular to the vertical direction. The maximum dimension of the diaper main body 110 before it is worn is not less than 225 mm and not more than 265 mm in the vertical direction from the waist opening part 120 to a bottom of the crotch part 103, and is not less than 180 mm and not more than 215 mm in the lateral direction.

Diaper Main Body

The diaper main body 110 includes an underpants formed outer cover 140 having a waist opening part 120 to be fixed to the trunk of a wearer and a pair of leg holes to be fixed to the legs of the wearer, and a substantially belt-like inner member 150 joined to the inner side of the outer cover 140, the inner member 150 extends from the ventral side (front side) to the dorsal side (back side) of the diaper main body 110 passing through between the leg holes 130. The outer cover 140 is formed by assembling a front part 101 to be positioned ventral to the wearer, a back part 102 to be positioned to dorsal to the wearer and a crotch part 103 which is joined to one edge of the front part 101 and one edge of the back part 102 and positioned between the legs of the wearer. In order to assemble the outer cover 140 and the inner member 150, heat sealing, ultrasonic sealing, hot-melt adhesives, and the like can be used. In addition, the diaper main body 110 is provided with a plurality of elastic members 170 extending in curves along the peripheral edges of each of the leg holes 130 toward the back part 102 from the front part 101 through the top side of the leg hole 130.

The diaper main body 110 is provided with the elastic cords 107 which are elastic at parts of the front part 101 and can be the back part 102 thereof, and put on a wearer in a state where these elastic cords 107 are pulled so as to closely adhere to the wearer's body. The diaper main body 110 is also provided with a plurality of waist bands 109 which are formed of elastic material extending along the waist opening part 120. The waist bands 109 are substantially parallel to the edge of the waist opening part 120. The elastic cords 107 are provided on both sides of the front part 101 and the back part 102 extending substantially straight in the lateral direction of the diaper main body 110 to be parallel to the waist bands 109. The elastic cords 107 and the waist bands 109 are disposed among a plurality of sheets constituting the outer cover 140, and joined in an extended state between the two sandwiching sheets by hot-melting. Furthermore, the side flaps 190 are provided on both sides of the diaper main body 110, each of the side flaps 190 is formed by joining one side edge of the front part 101 and one side edge of the back part 102. Each of the side flaps 190 has a fastening tape 195 to be used when the diaper 100 is worn, and designs or the like may be indicated on the front part 101 and the back part 102.

Outer Cover

The outer cover 140 has at least one sheet forming the outward form of the diaper main body 110. As these sheets, to ensure liquid containment, softness and comfortableness to the skin and breathability, non-woven fabric sheets such as span-bond non-woven fabrics, through-air non-woven fabrics composed of fibers of polyethylene, polypropylene, polyethylene terephthalate or the like, span-lace non-woven fabric, and composite sheets formed with an elastic and extensible non-woven fabric containing elastomer and copolymer and an elastic film may be used. Furthermore, a water-impermeable plastic film or a multi-ply sheet of these films can be also used. In this case, the breathability and moisture permeability of the plastic films can be ensured by extending them after mixing with fillers.

As the non-woven fabrics, non-woven fabrics formed with sheath-core-type composite fibers formed from fibers of polyolefin, polyester, polyamide and such, or a side-by-side-type composite fiber can be used. The method for manufacturing a non-woven fabric is not restricted, and span-bond, point-bond, through-air bond, chemical bond, melt-blown, span-lace and needle-punch methods can be used for example. In this case, the fiber diameter of a fiber used for a non-woven fabric is preferably 0.1 μm to 50 μm, more preferably 5 μm to 30 μm. The specific weight per unit area of non-woven fabrics is preferably 2 g/m² to 100 g/m², more preferably 7 g/m² to 20 g/m².

Furthermore, the outer cover 140 of the present embodiment has a liquid-impermeable back sheet. The back sheet prevents excretions once absorbed into an absorbent core from leaking to the outside. As the back sheet, a water-repellent non-woven fabric, moisture-permeable plastic film having minute pores or laminates thereof can be used. It is possible to reduce the stuffy feeling and dissipate the uncomfortable feeling when fixing a diaper by using moisture-permeable materials as the back sheet. As a material used for a moisture-permeable sheet, a membranous sheet-like film made of synthetic plastic and a breathable film obtained by filling up a synthetic plastic with a filler and subjecting it to a stretching treatment, a composite laminate formed of a paper and a non-woven fabric, a breathable blocking sheet with a 10% to 30% aperture ratio obtained by arranging capillaries having a pore diameter in the range of 0.1 mm to 0.6 mm opposing toward the absorbing body side or the like can be used. A thermoforming film embossed to confer a fabric-like outward appearance thereon is preferable.

Inner Member

The inner member 150 has an absorbent body 180 composed of an absorbent core and a liquid-permeable surface side sheet. The water absorption capacity and the water-holding capacity of the absorbing body 180 per diaper are 900 g and 600 g respectively, such that it has a more excellent absorption capacity than conventional products.

As a surface side sheet, a material which is not irritating to the skin is preferable, and liquid-permeable sheets such as hydrophilic non-woven fabric and porous plastic are used. Non-woven fabrics cited herein are those manufactured by the span-bond, span-lace, needle-punch, melt-blown, thermal bond, chemical bond, air-through methods, etc. As a non-woven fabric, the one similar to that for the outer cover 140 can be used. Furthermore, rayon, acetate, cotton, pulp or synthetic resin is used alone or as a composite fibrous sheet by combining them so as to form a core-sheath structure.

As an absorbent core one in which a fibrillated pulp and a super absorbent polymer are jointly employed is preferably used. In addition, absorbent cores in which cellulosic fibers, thermoplastic resin, super absorbent polymer, thermal bonding fibers and such are mixed and heat-treated are preferably used. The absorbent core can be formed by laminating the material mentioned above. In the case of an absorbent core having a plurality of layers, the super absorbent polymer may be disposed at any one of the upper, middle and lower layers, and it may be mixed with pulp to be disposed at any one of the upper, middle and lower layers. A super absorbent polymer is preferably the one capable of absorbing and retaining a liquid more than twenty times its own weight and having a property to become gelled. Examples of such super absorbent polymer are starch-acrylate (salt) graft copolymer, hydrolyzates of starch-acrylonitrile copolymer, cross-linked products of sodium carboxymethyl cellulose, acrylate (salt) polymer, etc.

Elastic Member

Figure 4:
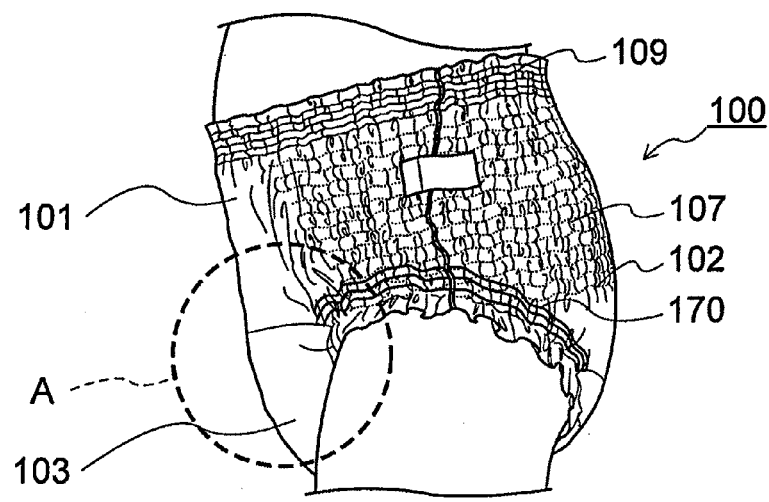
FIG. 4 is the underpants-type disposable diaper according to an embodiment viewed from the flank side of a wearer in a state soon after the diaper is worn.

The plural elastic members 170 are disposed along each of the peripheral edges of the leg holes 130 so as to extend in curves from the front part 101 to the back part 102 through the top side of the leg holes 130. The elastic members are provided in both the front part 101 and the back part 102, and each of the elastic member 170 extends from the top front of the leg hole 130 to the bottom rear of the leg hole 130 to form a substantially semicircular arc viewed from the side of the diaper 100 as shown in FIG. 4. The arrangements of the elastic members 170 provided in both sides of the front part 101 are devised in the present invention. Specifically, the elastic members 170 are provided in the front part 101 so that they extend from the side edge of the front part 101 toward the center of the front part 101 forming into horizontally elongated arc as shown in FIG. 2. One end of the elastic member 170 of the front part 101 is positioned near the side edge of the front part 101, and the other end (top point) of the elastic member 170 of the front part 101 is positioned near the joint portion joining the front part 101 and the crotch part 103.

More specifically, each of the elastic members 170 are provided at an area in which the ratio of the minimum dimension in the lateral direction from one end positioned at the side of the front part 101 to the top point of the elastic member 170 to the minimum dimension in the vertical direction is not less than 1.0 and not more than 3.0 in a state prior to wearing the diaper. That is, in FIG. 2, a plan view of the underpants-type disposable diaper 100 according to this embodiment, the value X/Y, which is the ratio of the minimum dimension X in the lateral direction from the end part of the front part 101 to the top point of the elastic member 170 to the minimum dimension Y in the vertical direction from a lowermost end of the elastic members 170 to an uppermost end of the elastic members 170, is within the range of not less than 1.0 and not more than 3.0.

Figure 7:
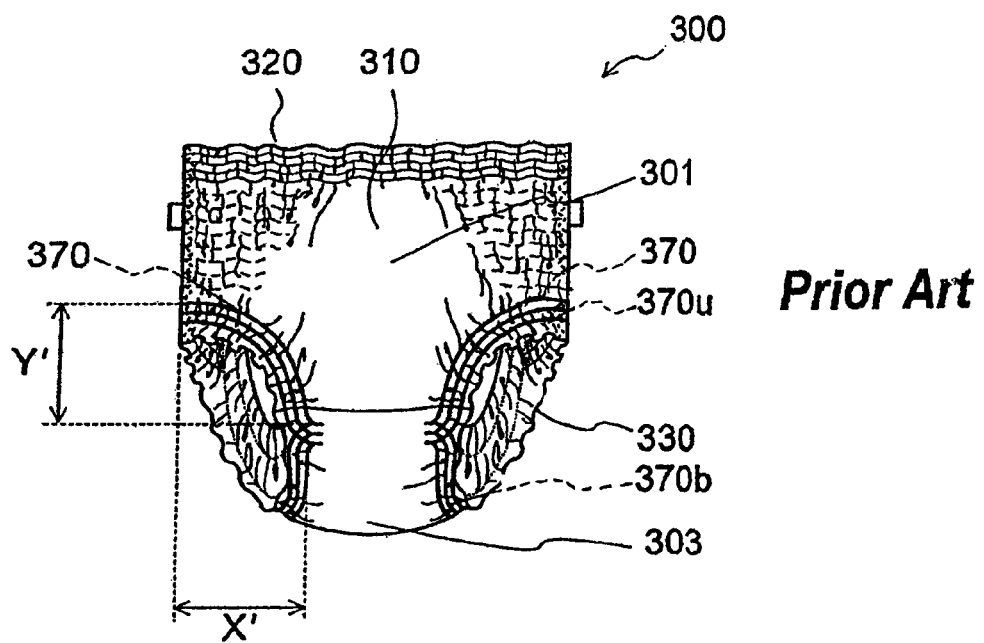
FIG. 7 is a plan view of the conventional underpants-type disposable diaper.
Figure 8:
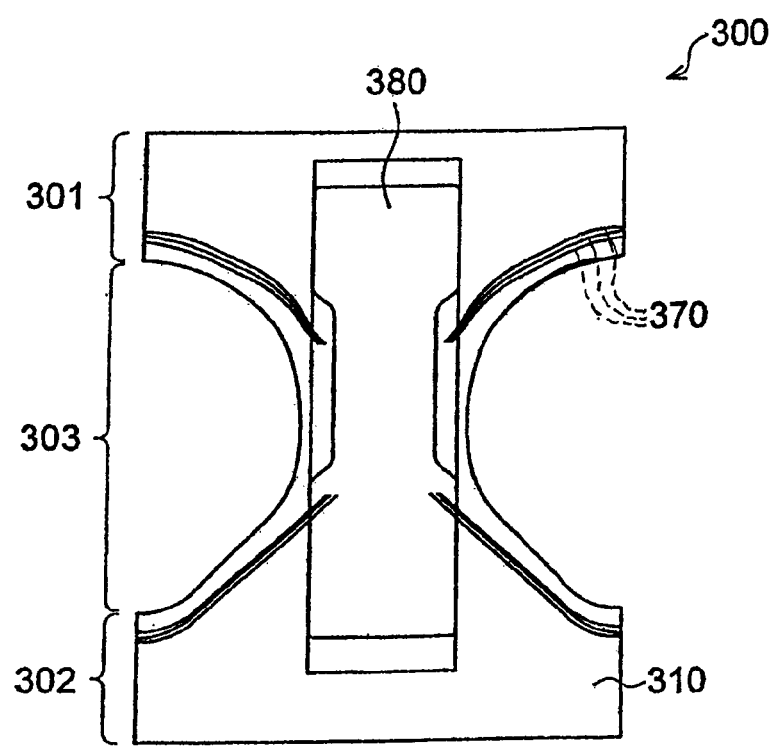
FIG. 8 is an exploded plan view of the conventional underpants-type disposable diaper whose side flap is opened to separate a front part and a back part
Figure 9:
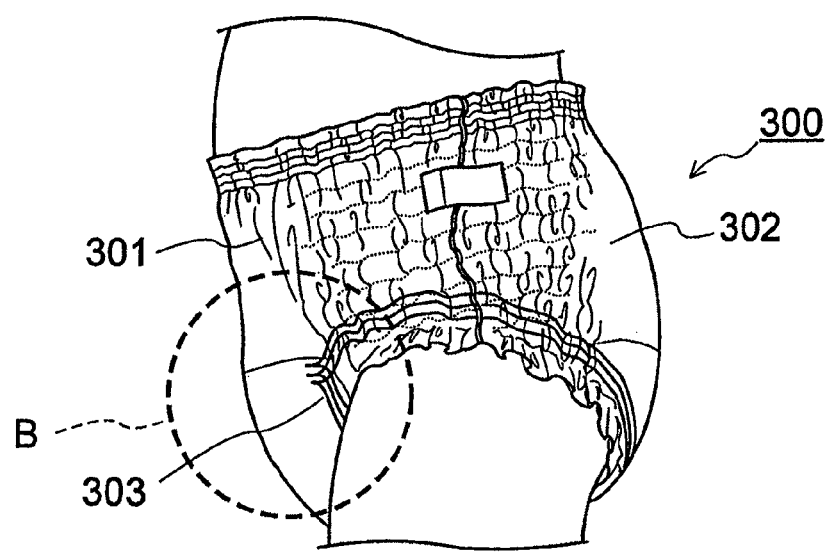
FIG. 9 is the conventional underpants-type disposable diaper viewed from the flank side of a wearer in a state soon after the diaper is worn.

In contrast to this, in a conventional underpants-type disposable diaper 300 as shown in FIG. 7, an elastic member 370 extends from the bottom front of a leg hole 330 toward the bottom rear of the leg hole forming into substantially circular arc as shown in FIG. 9. In particular, an elastic member (upper elastic member) 370*u* positioned mainly in a front part 301 and an elastic member (lower elastic member) 370*b* positioned mainly in a crotch part 303 are provided on the front side of the diaper 300. Each of the upper elastic members 370*u* extends from the upper groin portion positioned above the groin portion to the side of the front part 301, while each of the lower elastic members 370*b* extends from the lower groin portion positioned around the groin portion to the front part 301, and the top point of the upper elastic member 370*u* crosses one end of the lower elastic member 370*b* near the end of the front part 301. The value of the ratio X'/Y', the minimum dimension X' in the lateral direction to the minimum dimension Y' in the vertical direction from the crossing point of these elastic members to the other end of the upper elastic member 370*u* is in the range of 0.5 to 0.8. Thus, as is obvious from comparison of FIGS. 2 and 6, in the underpants-type disposable diaper 100 according to this embodiment, the elastic member 170 in the vertical direction is smaller in dimension than the conventional underpants-type disposable diaper 300 so that the elasticity thereof in the vertical direction above the groin portion is reduced.

As the elastic members 170, various materials such as rubber strings, flat rubber belts and rubber ribbon made of natural rubber, synthetic rubber and polyurethane, heat-shrinkage materials, and water-absorbent shrinkage fibers can be used, but are not particularly limited as long as they are sufficiently elastic. In this case, the intervals between the elastic members 170 at the top points thereof are not less than 7 mm and not more than 12 mm in a state prior to wearing the diaper, such that they are designed to be wider compared to the conventional products.

Water Absorption Capacity and Water-Holding Capacity

The "water absorption capacity" in the present invention refers to the maximum amount of water absorbable with the absorbent body, specifically to the amount of water maintainable therein when a 10 kg load is applied thereto. The "water-holding capacity" in this invention refers to the maximum amount of the absorbed water maintainable by the absorbent body, specifically to the amount of water maintainable therein when the absorbent body is dehydrated after centrifugation at 75 G. The water absorption capacity and water-holding capacity per diaper can be obtained by the following measuring methods.

First, a physiological saline (0.9% NaCl solution), an acrylic plate (320 mm×545 mm in the standard dimension, 3 mm ~5 mm in thickness, 400 g to 600 g in weight), two weights each of 5 kg weights, a dehydrator (75 G) and a wire net (standard wire net: 5 mm in pore diameter, 5 mm in distance between pores) are prepared as the tools and reagent to be used.

Next, samples of the object to be measured were collected. Specifically, after a piece of diaper was weighed, waist bands forming waist gathers (WG), elastic members forming leg gathers (LG) and elastic cords forming lateral side gather (LSG) were cut to flatten the diaper. When cutting the diaper, it is necessary to be cautious so as not to cut into the absorbent body. In this case, the number of samples to be prepared was fixed at 5 (n=5).

As a first procedure, the absorbent body of a diaper was immersed faced downward into about 20 liters of a physiological saline while pressing the diaper down with the hand. The physiological saline can be used for measuring up to 6 pieces of diaper, but is required to be replaced with a fresh one for measuring more than 6 pieces of samples due to the resulting concentration changes. After the diaper was immersed, it was left as it was for 30 minutes. After a lapse of 30 minutes, the diaper was taken out, mounted on a wire net with the absorbent body facing downward, and covered with the acrylic plate. Furthermore, two 5 kg weights were mounted on the acrylic plate so as to apply a 10 kg load in total, and the diaper was left with the loaded state for 20 minutes. After 20 minutes, the diaper was weighed, and the water absorption capacity was obtained from the difference between the weight after the application of the weight load and the initial weight of the diaper.

Next, the diapers (up to 3 pieces) treated as described above to measure the water absorption capacity were placed in a dehydrator with the absorbent bodies facing outward such that diapers were arranged not lying on one another and were dehydrated by centrifugation at 75 G for 90 second. After the dehydration, the diapers were weighed, and the water-holding capacity was obtained from the difference between the weight after the dehydration and the initial weight of the diaper.

Protrusion of the Groin Portion While the Diaper is Worn

Figure 5:
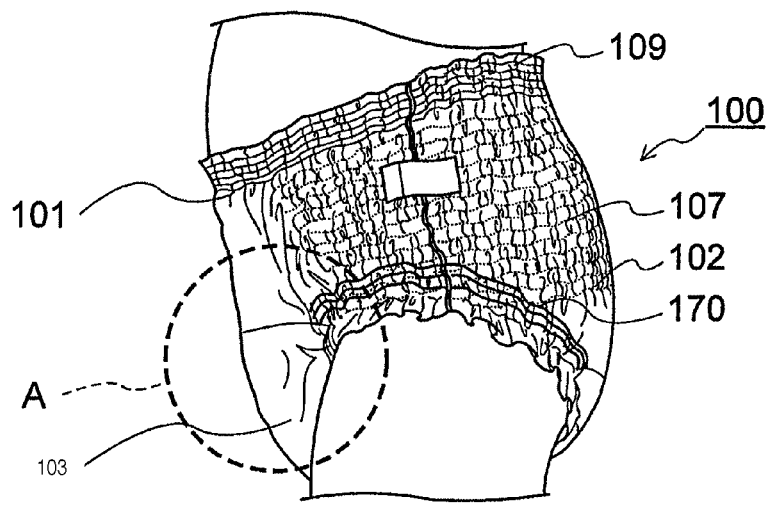
FIG. 5 is the underpants-type disposable diaper according to an embodiment in its use viewed from the flank side of a wearer.
Figure 10:
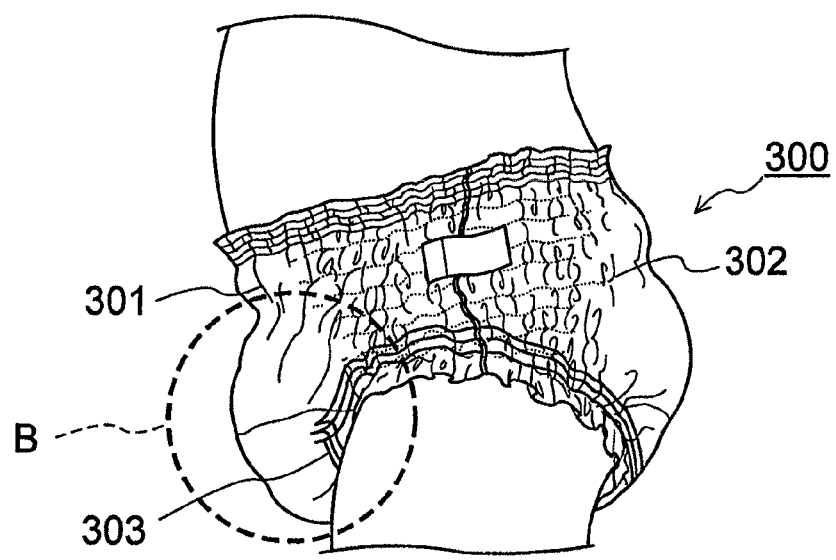
FIG. 10 is the state of the conventional underpants-type disposable diaper in its use viewed from the flank side of a wearer.

The states of the underpants-type disposable diaper 100 according to this embodiment viewed from the side of a wearer soon after it is put on (hereinafter referred to as "beginning of use") and after for a prolonged period (hereinafter referred to as "in use") are shown in FIGS. 4 and 5. Similarly, the states of the conventional underpants-type disposable diaper 300 viewed from the side of a wearer at the beginning of use and in use are shown in FIGS. 9 and 10. As is obvious from these figures, in the conventional underpants-type disposable diaper 300, it can be clearly confirmed that the section around the groin B is protruded after the diaper has absorbed fluid. In contrast, in the underpants-type disposable diaper 100 according to this embodiment, not much difference in its state has been observed even after it has absorbed fluid, such that it can be confirmed that the protrusion of the section around the groin A is prevented.

What is claimed is:

1. An underpants-type disposable diaper, comprising an underpants-formed diaper main body, wherein said diaper main body comprises:
    an underpants-formed outer cover having
        a waist opening part extending in a lateral direction of the diaper main body and adapted to surround a wearer's trunk; and
        a pair of leg holes for the wearer's legs to pass through;
    the outer cover further including
        a front part to be positioned on a front side of the wearer and having two side edges opposite to each other in the lateral direction;
        a back part to be positioned on a back side of the wearer; and
        a crotch part joined to said front part and said back part and adapted to be positioned between the legs of the wearer;
    a substantially belt-shaped inner member directly joined to said outer cover on a skin-facing side of the diaper main body and having an absorbent body positioned between said leg holes;
    a plurality of waist bands formed of elastic material and extending along the waist opening part;
    elastic cords extending substantially straight in the front part and the back part, and parallel to the plurality of waist bands; and
    a group of elastic members positioned in the front part and the back part to form a continuous and substantially semicircular arc along each of the leg holes when viewed from a side of the diaper,
    wherein
    said group of elastic members in the front part has a first segment extending in the lateral direction from a corresponding one of the side edges of the front part and substantially parallel to a waist opening edge, and a second segment continuously extending in a curve from the first segment toward a center of the front part,
    the front part and the crotch part are separate pieces attached to each other at a joint portion,
    said group of elastic members has a first end adjacent to the joint portion and a second end adjacent to the corresponding side edge of the front part, and
    each of the elastic members is configured as a laterally elongated curve when said inner member is pulled in a direction around the wearer's trunk,
    wherein said group of the elastic members in the front part has a value X/Y, and the value X/Y is within a range of not less than 1.0 and not more than 3.0, where
        X is a minimum dimension in the lateral direction from the first end of the elastic members in the front part to the second end of the elastic members, and
        Y is a minimum dimension in a vertical direction perpendicular to the lateral direction from a lowermost end of the elastic members in the front part to an uppermost end of the elastic members.

2. An underpants-type disposable diaper, comprising an underpants-formed diaper main body, wherein said diaper main body comprises:
    an underpants-formed outer cover having
        a waist opening part extending in a lateral direction of the diaper main body and adapted to surround a wearer's trunk; and
        a pair of leg holes for the wearer's legs to pass through;
    the outer cover further including
        a front part to be positioned on a front side of the wearer and having two side edges opposite to each other in the lateral direction;
        a back part to be positioned on a back side of the wearer; and
        a crotch part joined to said front part and said back part and adapted to be positioned between the legs of the wearer;
    a substantially belt-shaped inner member directly joined to said outer cover on a skin-facing side of the diaper main body, said inner member having an absorbent body positioned between said leg holes;
    a plurality of waist bands formed of elastic material and extending along the waist opening part;
    elastic cords extending substantially straight in the front part and the back part, and parallel to the plurality of waist bands; and
    a group of linear elastic members overlapping the elastic cords and extending from a top front of a peripheral edge of each of the leg holes in the front part to a bottom rear of the peripheral edge of the leg hole in the back part to form a substantially laterally elongated curve along each of the leg holes as viewed from a side of the diaper;
    wherein
    the front part and the crotch part are separate pieces attached to each other at a joint portion,
    said group of elastic members has a first end adjacent to the joint portion and a second end adjacent to the corresponding side edge of the front part,
    wherein said group of elastic members in the front part has a value X/Y, and the value X/Y is within a range of not less than 1.0 and not more than 3.0, where X is a minimum dimension in the lateral direction from the first end of the elastic members in the front part to the second end of the elastic members, and Y is a minimum dimension in a vertical direction perpendicular to the lateral direction from a lowermost end of the elastic members in the front part to an uppermost end of the elastic members, and wherein the inner member is inelastizied along the peripheral edge of each of the leg holes, wherein the group of elastic members in the front part has
a first segment extending in the lateral direction at the top front of the peripheral edge of each of the leg holes and substantially parallel to a waist opening edge, and
a second segment continuously extending at the bottom rear of the peripheral edge of the leg hole.

3. The underpants-type disposable diaper according to claim 1, wherein:
a maximum dimension of said diaper main body in the vertical direction is not less than 225 mm and not more than 265 mm in a state prior to its wearing, and a maximum dimension of said diaper main body in the lateral direction is not less than 180 mm and not more than 215 mm in the state prior to its wearing;
an interval between ends of the elastic members positioned near the center of said front part is not less than 7 mm and not more than 12 mm in the state prior to its wearing.

4. The underpants-type disposable diaper according to claim 2, wherein:
a maximum dimension of said diaper main body in the vertical direction is not less than 225 mm and not more than 265 mm in a state prior to its wearing, and a maximum dimension of said diaper main body in the lateral direction is not less than 180 mm and not more than 215 mm in the state prior to its wearing;
an interval between ends of the elastic members positioned near the center of said front part is not less than 7 mm and not more than 12 mm in the state prior to its wearing.

5. The underpants-type disposable diaper according to claim 1, wherein said group of elastic members allows a water absorption capacity of said absorbent body not less than 800 g and not more than 1000 g and a water-holding capacity of said absorbent body not less than 500 g and not more than 700 g without a protrusion of a groin portion positioned around said inner member.

6. The underpants-type disposable diaper according to claim 2, wherein said group of elastic members allows a water absorption capacity of said absorbent body not less than 800 g and not more than 1000 g, and a water-holding capacity of said absorbent body not less than 500 g and not more than 700 g without a protrusion of a groin portion positioned around said inner member.

7. The underpants-type disposable diaper according to claim 3, wherein said group of elastic members allows a water absorption capacity of said absorbent body is not less than 800 g and not more than 1000 g, and a water-holding capacity of said absorbent body not less than 500 g and not more than 700 g without a protrusion of a groin portion positioned around said inner member.

8. The underpants-type disposable diaper according to claim 4, wherein said group of elastic members allows a water absorption capacity of said absorbent body is not less than 800 g and not more than 1000 g, and a water-holding capacity thereof is not less than 500 g and not more than 700 g without a protrusion of a groin portion positioned around said inner member.

9. The underpants-type disposable diaper according to claim 1, wherein said group of elastic members does not extend into the crotch part.

10. The underpants-type disposable diaper according to claim 2, wherein said group of elastic members does not extend into the crotch part.

11. An underpants-type disposable diaper, comprising an underpants-formed diaper main body, wherein said diaper main body comprises:
an outer cover having
a waist opening part extending in a lateral direction of the diaper main body and adapted to surround a wearer's trunk; and
a pair of leg holes for the wearer's legs to pass through;
the outer cover further including
a front part to be positioned on a front side of the wearer and having two side edges opposite to each other in the lateral direction;
a back part to be positioned on a back side of the wearer; and
a crotch part joined to said front part and said back part and adapted to be positioned between the legs of the wearer;
a substantially belt-shaped inner member directly joined to said outer cover on a skin-facing side of the diaper main body and having an absorbent body positioned between said leg holes;
a plurality of waist bands formed of elastic material and extending along the waist opening part;
elastic cords extending substantially straight in the front part and the back part and parallel to the plurality of waist bands; and
front and back groups of elastic members positioned in the front part and the back part, respectively, each elastic member forming a continuous and substantially semicircular arc along each of the leg holes when viewed from a side of the diaper,
wherein
said front group of elastic members in the front part extends from the side edges of the front part toward a center of the front part,
said front group of elastic members in the front part has
a first segment extending in the lateral direction from the corresponding side edge of the front part and substantially parallel to a waist opening edge, and
a second segment continuously extending in a curve from the first segment toward the center of the front part,
the front part and the crotch part are separate pieces attached to each other at a joint portion,
said front group of elastic members has a first end adjacent to the joint portion and a second end adjacent to the corresponding side edge of the front part, and
each of the elastic members is configured as a laterally elongated arc when said inner member is pulled in a direction around the wearer's trunk,
said front group of the elastic members in the front part has a value X/Y falling within a range of not less than 1.0 and not more than 3.0, where
X is a minimum dimension in the lateral direction from the first end of the elastic members in the front part to the second end of the elastic members, and
Y is a minimum dimension in a vertical direction perpendicular to the lateral direction from a lowermost end of the elastic members in the front part to an uppermost end of the elastic members, and a peripheral edge of the inner member along each of the pair of the leg holes in the crotch part is free of elastic members.

12. The underpants-type disposable diaper according to claim 11, wherein a maximum dimension of said diaper main body in the vertical direction is not less than 225 mm and not more than 265 mm in a state prior to its wearing, and a maximum dimension of said diaper main body in the lateral direction is not less than 180 mm and not more than 215 mm in the state prior to its wearing;

an interval between ends of the elastic members positioned near the center of said front part is not less than 7 mm and not more than 12 mm in the state prior to its wearing.

13. The underpants-type disposable diaper according to claim 11, wherein said front and back groups of the elastic members allow a water absorption capacity of said absorbent body not less than 800 g and not more than 1000 g, and a water-holding capacity of said absorbent body not less than 500 g and not more than 700 g without a protrusion of a groin positioned around said inner member.

14. The underpants-type disposable diaper according to claim 12, wherein said front and back groups of the elastic members allow a water absorption capacity of said absorbent body not less than 800 g and not more than 1000 g, and a water-holding capacity of said absorbent body not less than 500 g and not more than 700 g without a protrusion of a groin portion positioned around said inner member.

15. The underpants-type disposable diaper according to claim 11, wherein said front and back groups of the elastic members do not extend into the crotch part.

16. The underpants-type disposable diaper according to claim 1, wherein the group of elastic members in the front part extends along an upper side of each of the leg holes and terminates near the joint portion joining the front part and the crotch part without extending into a lower side of the leg hole.

17. The underpants-type disposable diaper according to claim 2, wherein the group of elastic members in the front part does not extend along a bottom rear of the peripheral edge of each of the leg holes.

18. The underpants-type disposable diaper according to claim 1, wherein the joint portion where the front and crotch parts are attached together extends, in the lateral direction, from the peripheral edge of one of the leg holes to the peripheral edge of the other leg hole, and the group of elastic members terminates adjacent the joint portion.

19. The underpants-type disposable diaper according to claim 2, wherein the joint portion where the front and crotch parts are attached together extends, in the lateral direction, from the peripheral edge of one of the leg holes to the peripheral edge of the other leg hole, and the group of elastic members terminates adjacent the joint portion.

20. The underpants-type disposable diaper according to claim 11, wherein the joint portion where the front and crotch parts are attached together extends, in the lateral direction, from the peripheral edge of one of the leg holes to the peripheral edge of the other leg hole, and the front and back groups of elastic members terminate adjacent the joint portion.

21. The underpants-type disposable diaper according to claim 1, wherein an entire dimension of the first segment in the lateral direction is greater than that of the second segment.

22. The underpants-type disposable diaper according to claim 1, wherein the front part is directly joined to an edge of the crotch part to define the joint portion, and the first end of said group of elastic members is adjacent to the edge of the crotch part.

23. The underpants-type disposable diaper according to claim 2, wherein the front part is directly joined to an edge of the crotch part to define the joint portion, and the first end of said group of elastic members is adjacent to the edge of the crotch part.

24. The underpants-type disposable diaper according to claim 11, wherein the front part is directly joined to an edge of the crotch part to define the joint portion, and the first end of said front group of elastic members is adjacent to the edge of the crotch part.

25. The underpants-type disposable diaper according to claim 1, wherein the inner member is inelastizied along the peripheral edge of each of the leg holes.

* * * * *